United States Patent
Wang et al.

(10) Patent No.: US 9,036,018 B2
(45) Date of Patent: May 19, 2015

(54) FACIAL EXPRESSION RECOGNITION SYSTEMS AND METHODS AND COMPUTER PROGRAM PRODUCTS THEREOF

(75) Inventors: Wen-Nan Wang, Cingshuei Township, Taichung County (TW); Shang-Hong Lai, Hsinchu (TW); Chia-Te Liao, Kaohsiung (TW); Hui-Ju Chuang, Kaohsiung (TW); Tzu-Chen Tsai, Taichung (TW); Fang-kai Chang, Chiayi (TW)

(73) Assignee: INSTITUTE FOR INFORMATION INDUSTRY, Taipei (TW)

( * ) Notice: Subject to any disclaimer, the term of this patent is extended or adjusted under 35 U.S.C. 154(b) by 1023 days.

(21) Appl. No.: 13/116,724

(22) Filed: May 26, 2011

(65) Prior Publication Data

US 2011/0310237 A1   Dec. 22, 2011

(30) Foreign Application Priority Data

Jun. 17, 2010  (TW) ................................ 99119644 A (51) Int. Cl.
*H04N 7/18*   (2006.01)
*A61B 1/04*   (2006.01)
(Continued)

(52) U.S. Cl.
CPC  *H04N 7/18* (2013.01); *A61B 1/041* (2013.01); *A61B 1/00036* (2013.01); *G06K 9/00315* (2013.01)

(58) Field of Classification Search
CPC ....... A61B 1/041; A61B 1/00036; H04N 7/18
USPC ........................................... 348/77; 345/420
See application file for complete search history.

(56) References Cited

U.S. PATENT DOCUMENTS 6,072,496 A * 6/2000 Guenter et al. ............... 345/419
6,492,986 B1 * 12/2002 Metaxas et al. ............... 345/420
(Continued)

FOREIGN PATENT DOCUMENTS

TW   200947316   11/2009
TW   201028934   8/2010

OTHER PUBLICATIONS

Chinese language office action dated Jul. 25, 2012.
(Continued)

*Primary Examiner* — Shawn An
(74) *Attorney, Agent, or Firm* — McClure, Qualey & Rodack, LLP (57) ABSTRACT

A facial expression recognition system includes a facial database, an image capture unit, an expression recognition data generation unit and an expression recognition unit. The facial database includes a plurality of expression information and expression features of optical flow field, wherein each of the expression features of optical flow field corresponds to one of the expression information. The image capture unit captures a plurality of facial images. The expression recognition data generation unit is coupled to the image capture unit and the facial database for receiving a first facial image and a second facial image from the image capture unit and calculating an expression feature of optical flow field between the first facial image and the second facial image corresponding to each of the expression information. The expression recognition unit is coupled to the expression recognition data generation unit for determining a facial expression corresponding to the first and second facial images according to the calculated expression feature of optical flow field for each of the expression information and the variation features in optical flow in the facial database.

18 Claims, 7 Drawing Sheets

(51) Int. Cl.
*A61B 1/00* (2006.01)
*G06K 9/00* (2006.01)

(56) References Cited

U.S. PATENT DOCUMENTS

| | | | |
|---|---|---|---|
| 6,879,323 B1 * | 4/2005 | Nagai et al. | 345/420 |
| 6,879,709 B2 * | 4/2005 | Tian et al. | 382/118 |
| 8,219,438 B1 * | 7/2012 | Moon et al. | 705/7.29 |

OTHER PUBLICATIONS

English language translation of abstract of TW 201028934 (published Aug. 1, 2010, p. 3 of publication).

Tang, L., et al.; "Weighted Modular 2D PCA-Based Face Recognition from a Single Sample Image Per Class;" Journal of Image and Graphics; vol. 13; No. 12; Dec. 2008; pp. 2307-2313.

English language translation of abstract of "Weighted Modular 2D PCA-Based Face Recognition from a Single Sample Image Per Class."

Taiwanese language office action dated Jul. 25, 2013.

Pan, Y.A.; "Automatic Facial Expression Recognition System in Low Resolution Image Sequence"(Master Thesis); National Cheng Kung University; Jul. 2004.

English language translation of abstract of TW 200947316 (p. 3, published Nov. 16, 2009).

* cited by examiner

FACIAL EXPRESSION RECOGNITION SYSTEMS AND METHODS AND COMPUTER PROGRAM PRODUCTS THEREOF

CROSS REFERENCE TO RELATED APPLICATIONS

This Application claims priority of Taiwan Application No. 099119644, filed on Jun. 17, 2010, the entirety of which is incorporated by reference herein.

BACKGROUND OF THE INVENTION

1. Field of the Invention

The invention relates to facial expression recognition systems and methods thereof, and more particularly to facial expression recognition systems and methods thereof capable of recognizing the facial expression of a plurality of facial images.

2. Description of the Related Art

With development of visual technology, many human-machine interaction mechanisms have been achieved by utilizing visual detection and recognition technology. For example, mobile robot interaction mechanisms (including automatic following), safe monitoring mechanisms and so on.

As to dynamic or static facial databases, the main work of an automated human facial recognition system consists of utilizing a facial image database to recognize one or more humans so as to serve as identifying or recognizing expression features. To achieve this objective, at first, the facial portion in the image has to be captured out of the image; and then a captured facial feature has to be performed to serve as a basis for comparison.

In the field of the human facial recognition, the most difficult technological challenge consists because a human face has numerous expressions/motion variations which may affect the accuracy of facial recognition. Thus, it is difficult to build a human facial recognition system having high recognizability and accuracy. In addition, for certain applications, it is also very important to recognize human emotions/facial expression using the facial image.

A conventional technology for recognizing facial expression by video sequence includes: detecting the human face and locating the human facial feature points by utilizing the automatic emotion feature point tracer; then, building feature for facial expression in accordance with the apparent motion vectors of facial feature points; and then classifying the features by a classifier. However, there are many variations in size, direction, light and background for the facial images retrieved from the video sequence, and poses, dressings, incomplete visibility of human faces, rotation angles and statuses of retrieved facial images may also affect the detection of the feature points. If the feature points of the retrieved facial images can not be successfully acquired, variations of the eyes and the mouth of the user in the continuous images can not be found, resulting in the failure of recognizing facial expression.

Further, because the facial expression of the users have detailed variations and may be different from person to person, which is difficult to be specially defined and descried, it is not easy to find the most discriminating expression information to determine facial expressions.

BRIEF SUMMARY OF THE INVENTION

It is therefore an objective to provide facial expression recognition systems and methods thereof.

In one embodiment, a facial expression recognition method is provided. The method comprises the following steps. First, a first facial image and a second facial image are received. Next, an expression feature of optical flow field between the first facial image and the second facial image corresponding to each of a plurality of expression information respectively is calculated. Then, a facial expression corresponding to the facial images is determined according to the calculated expression feature of optical flow field for each of the plurality of expression information and a plurality of the expression features of optical flow field in a facial database, wherein the facial database comprises the plurality of expression information and the plurality of expression features of optical flow field, and wherein each of the expression features of optical flow field corresponds to one of the plurality of expression information.

Another embodiment of a facial expression recognition system comprises a facial database, an image capture unit, an expression recognition data generation unit and an expression recognition unit. The facial database includes a plurality of expression information and a plurality of expression features of optical flow field, wherein each of the expression features of optical flow field corresponds to one of the plurality of expression information. The image capture unit captures a plurality of facial images. The expression recognition data generation unit is coupled to the image capture unit and the facial database for receiving a first facial image and a second facial image from the image capture unit and calculating an expression feature of optical flow field between the first facial image and the second facial image corresponding to each of the plurality of expression information. The expression recognition unit is coupled to the expression recognition data generation unit for determining a facial expression corresponding to the first and second facial images according to the calculated expression feature of optical flow field for each of the plurality of expression information and the variation features in optical flow in the facial database.

Another embodiment of a facial expression recognition apparatus includes a shell, a facial database, an image capture unit, an expression recognition data generation unit, an expression recognition unit and a display unit. The shell may internally contain the facial database, the image capture unit, the expression recognition data generation unit and the expression recognition unit while the display unit may be disposed outside of the shell or may link to the expression recognition unit within the shell through a wired/wireless connection. The facial database is disposed inside of the shell and includes a plurality of expression information and a plurality of expression features of optical flow field, wherein each of the expression features of optical flow field corresponds to one of the plurality of expression information. The image capture unit is disposed inside of the shell and captures a plurality of facial images. The expression recognition data generation unit is disposed inside of the shell and is coupled to the image capture unit and the facial database for receiving a first facial image and a second facial image from the image capture unit and calculating an expression feature of optical flow field between the first facial image and the second facial image corresponding to each of the plurality of expression information respectively. The expression recognition unit is disposed inside of the shell and is coupled to the expression recognition data generation unit for determining a facial expression corresponding to the facial images according to the calculated expression feature of optical flow field for each of the plurality of expression information and the variation features in optical flow in the facial database. The display unit is disposed outside of the shell and is coupled to the expression recognition unit for displaying a result corresponding to the determined facial expression.

Facial expression recognition methods and systems may take the form of a program code embodied in a tangible media. When the program code is loaded into and executed by a machine, the machine becomes an apparatus for practicing the disclosed method.

BRIEF DESCRIPTION OF THE DRAWINGS

The invention will become more fully understood by referring to the following detailed description with reference to the accompanying drawings, wherein.

DETAILED DESCRIPTION OF THE INVENTION

The following description is of the best-contemplated mode of carrying out the invention. This description is made for the purpose of illustrating the general principles of the invention and should not be taken during a limiting sense. The scope of the invention is best determined by reference to the appended claims.

Embodiments of the invention provide a facial expression recognition system and method thereof, in which a facial expression is determined by expression features of optical flow field stored in a facial database and the expression features of optical flow field between two or more facial images. Furthermore, the facial database may collect a large amount of facial expression image data in advance to serve as the training data and record the variation in the optical flow corresponding to each expression. In addition, each facial area of each expression, by learning and training, can be weighted in accordance with its importance level to generate a weighted mask for each expression so as to find out the most discriminating expression feature of optical flow field of each expression to use as a basis for determining the facial expression shown on a face of a user in the video sequence. Furthermore, among the received facial images, the nostril image can serve as a datum point to perform a calibration to more accurately find out the human facial feature (such as eyes, mouth and so on) which is able to recognize human emotions to perform the facial expression recognition.

Figure 1:
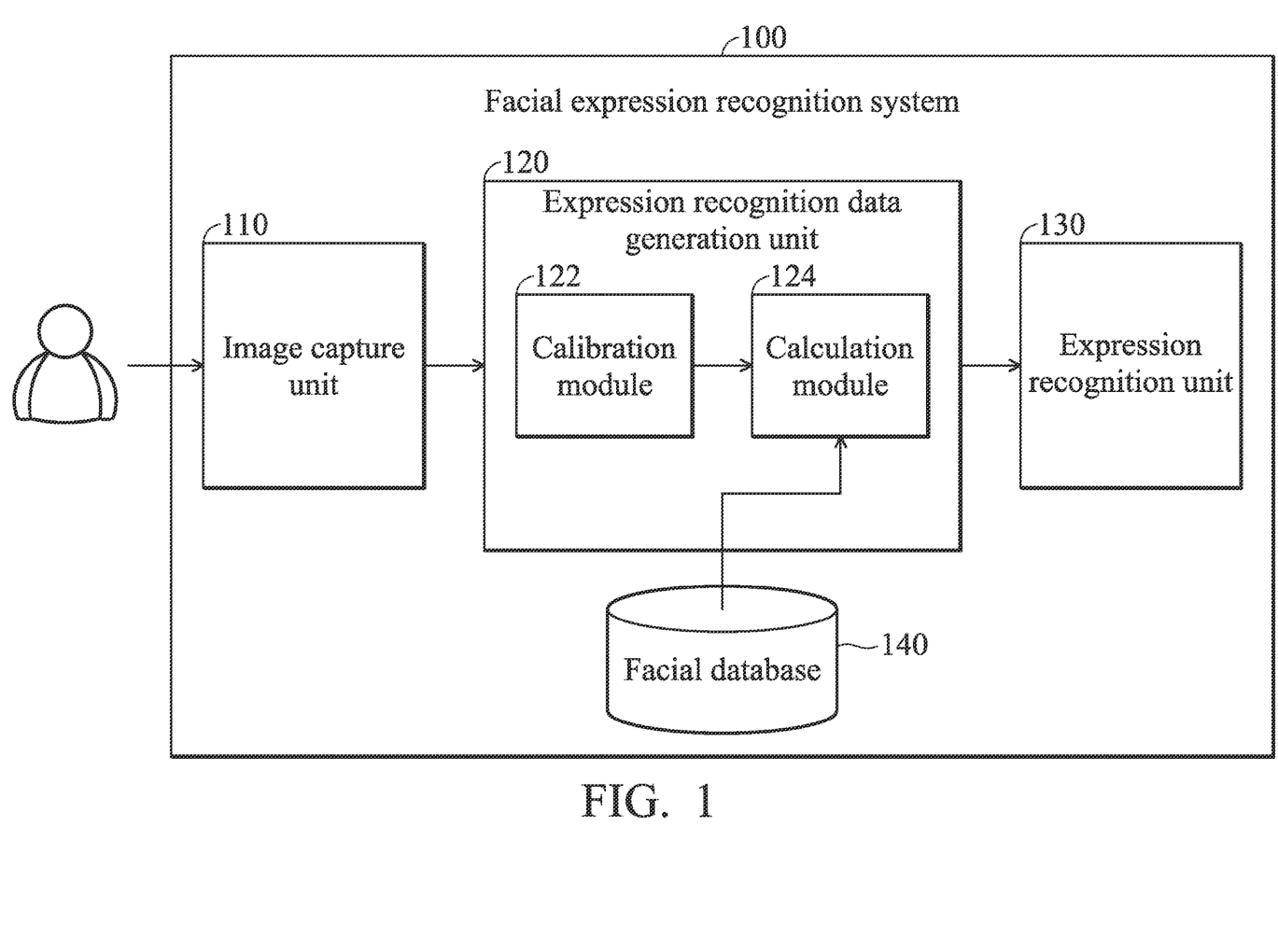
FIG. 1 is a schematic diagram illustrating an embodiment of a facial expression recognition system of the invention.

FIG. 1 is a schematic diagram illustrating an embodiment of a facial expression recognition system 100 of the invention. The facial expression recognition system 100 may be configured on a portable device or a computing device, such as a mobile phone, a PDA, a GPS navigation device, a laptop computer or any kind of computer systems, for performing the facial expression image recognition. The facial expression recognition system 100 at least comprises an image capture unit 110, a facial expression recognition data generation unit 120, an expression recognition unit 130 and a facial database 140. The image capture unit 110 can be used to receive or detect a facial image. For example, the image capture unit 110 may be variant types of video camera, camera or any photography apparatus capable of shooting the facial images. If the image capture unit 110 is a camera, it can capture two or more than two facial images in a certain period of time (for example, 0.5-3 seconds), and send them to the expression recognition data generation unit 120. If the image capture unit 110 is a video camera, it can, in a certain period of time, capture a continuous facial video sequence from which two or more than two facial images can be captured. Generally, a video sequence can be composed of multiple frames, for example, 30 frames. The facial image is used to recognize facial expressions such as surprise, anger, sad, happiness, disgust or a normal expression.

The expression recognition data generation unit 120 which is coupled to the image capture unit 110 may receive a first facial image and a second facial image from the image capture unit 110 and then calculate an expression feature of optical flow field between the first facial image and the second facial image. A calculation module 124 (described below) is utilized to convert the calculated expression feature of optical flow field and the expression features of optical flow field corresponding to the expression information in the facial database 140 to corresponding features, wherein the facial database 140 has a plurality of expression information and a plurality of expression features of optical flow field with each expression feature of optical flow field corresponding to one of the expression information. Data of the expression features of optical flow field of the facial database 140 may be created in advance. For example, a variation in optical flow between two facial images which represent a specific expression information can be found based on previously collected facial images. The found variation in optical flow may be further processed by a weighting mask process to obtain a variation feature in variation flow of the specific expression. For example, a variation in optical flow for the expression "smile" may be calculated by a facial image with the expression "smile" and a facial image without expression. Assume that the facial important area corresponding to the expression information "smile" could be the corners of the mouth and the eyes of a human, wherein the facial important area can be particularly weighted to serve as the expression feature of optical flow field for the expression information "smile". Note that each of the expression information may further include multiple representative samples (e.g. the expression information "smile" may include multiple types or different expressions for different people) so that each of the expression information may include multiple variations in optical flow so as to generate the plurality of expression features of optical flow field. In other embodiments, a number of most discriminating smile facial images which are facial images with the same expression information "smile" can be calculated to generate a representative expression feature of optical flow field for representing the expression information "smile". The expression recognition unit 130 may determine a corresponding facial expression by comparing the calculated expression feature of optical flow field between the first facial image and the second facial image with the expression features of optical flow field corresponding to the expression information in the facial database 140. For example, a expression feature of optical flow field that is most similar to the expression features of optical flow field between the first facial image and the second facial image is found among the variation features in optical flow in the facial database 140 and it is then determined that the facial expression corresponding to the facial images is the expression information which corresponds to the most similar expression feature of optical flow field.

Methods and related algorithms for detecting and obtaining facial images, for when the video sequence captured by the image capture unit 110 are continuous video images captured in a certain period of time, are well known in the art, thus detailed description is omitted here. For example, in one embodiment, a conventional algorithm, such as AdaBoost, may be used to detect and obtain the facial image so as to extract the facial portion from a complex image, but it is not limited thereto.

The optical flow represents the pixel displacement relationship between two corresponding images. In the embodiments of the invention, the expression feature of optical flow field generated by the facial expression variation can be served as a main feature for feature calculation. With this method, the brightness variation and the corresponding relationship between a facial image without expression and a facial image with expressions may be estimated at the same time.

Figure 5:
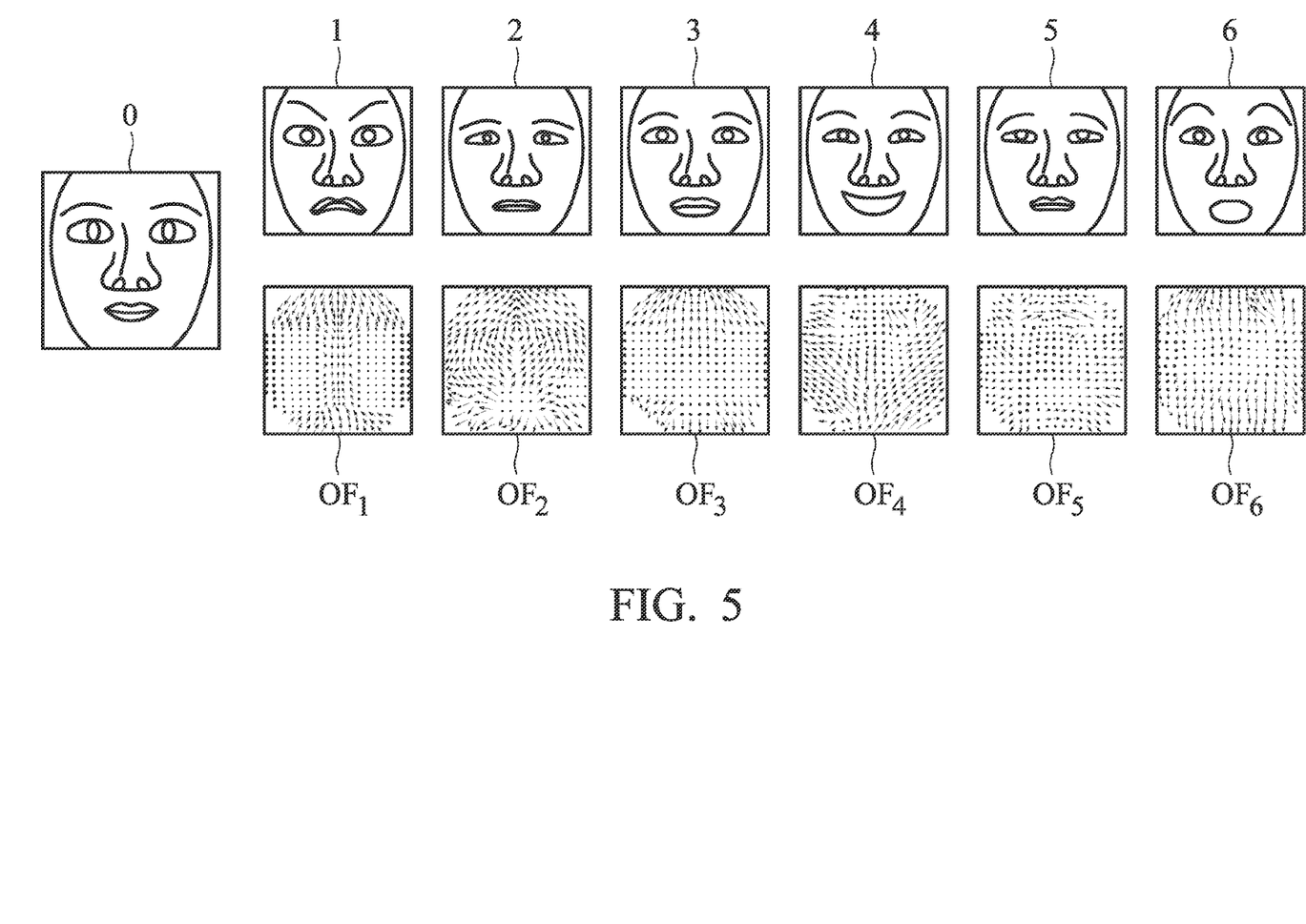
FIG. 5 is a schematic diagram illustrating an embodiment of an averaged expression face together with its corresponding expression optical flow of the invention.

The expression recognition data generation unit 120 calculates the expression feature of optical flow field between the first and the second facial images by utilizing the optical flow to calculate the motion vector of the facial muscle corresponding to the expression so as to extract the expression information feature which serves as a basis for determining the expression, as shown in FIG. 5. The method for calculating the variation in the optical flow of facial images will be illustrated below.

The expression recognition data generation unit 120 may further include a calibration module 122 and a calculation module 124, wherein the calibration module 122, when the expression feature of optical flow field between the first and the second images is calculated, may be used to perform a facial calibration to adjust the first and the second facial images to facilitate performing a subsequent calculation of the expression features of optical flow field. The calculation module 124 may first calculate the expression feature of optical flow field between the first and the second images and then utilize the weight masks, each corresponding to the different facial expressions, to perform a weighted operation on the calculated variation in optical flow to obtain the expression feature of optical flow field.

The expression recognition unit 130 is coupled to the expression recognition data generation unit 120 and may analysis or classify what the facial expression is corresponding to the video sequence according to the expression features of optical flow field from the expression recognition data generation unit 120 and the expression features of optical flow field in the facial database 140, such as determining whether the facial expression belongs to a surprised, angry, sad, happy, disgusted, normal expression and so on, so as to determine the facial expression corresponding to the facial images. In one embodiment, the expression recognition unit 130 may be, for example, a classifier such as a support vector machine (SVM), but is not limited thereto.

In another embodiment, the facial expression corresponding to the facial images may also be determined based on the expression features of optical flow field directly. If a calculated expression feature of optical flow field is similar to one of the expression features of optical flow field in the facial database, then it is determined that the facial expression corresponding to the facial image is the expression corresponding to the similar one of the expression feature of optical flow field. For example, if the calculated expression feature of optical flow field is similar to one of the variation features in optical flow in the facial database and the similar one of the expression features of optical flow field corresponds to the expression information "smile", then it is determined that the facial expression corresponding to the video sequence is "smile".

Furthermore, the system 100 may further comprise a display unit (not shown in FIG. 1) for displaying the result corresponding to the facial expression by way of, for example, a facial expression symbol, a facial expression word, a color, an animation or a photograph. The display unit may be any kind of screen or monitor which is coupled to the expression recognition unit 130 of the system 100 by a connecting line such as wired/wireless communication network or RS232. The system 100 may further comprise a speaker unit (not shown in FIG. 1) which plays the result corresponding to facial expression by voice, a sound of singing, music, or other voice.

Figure 2:
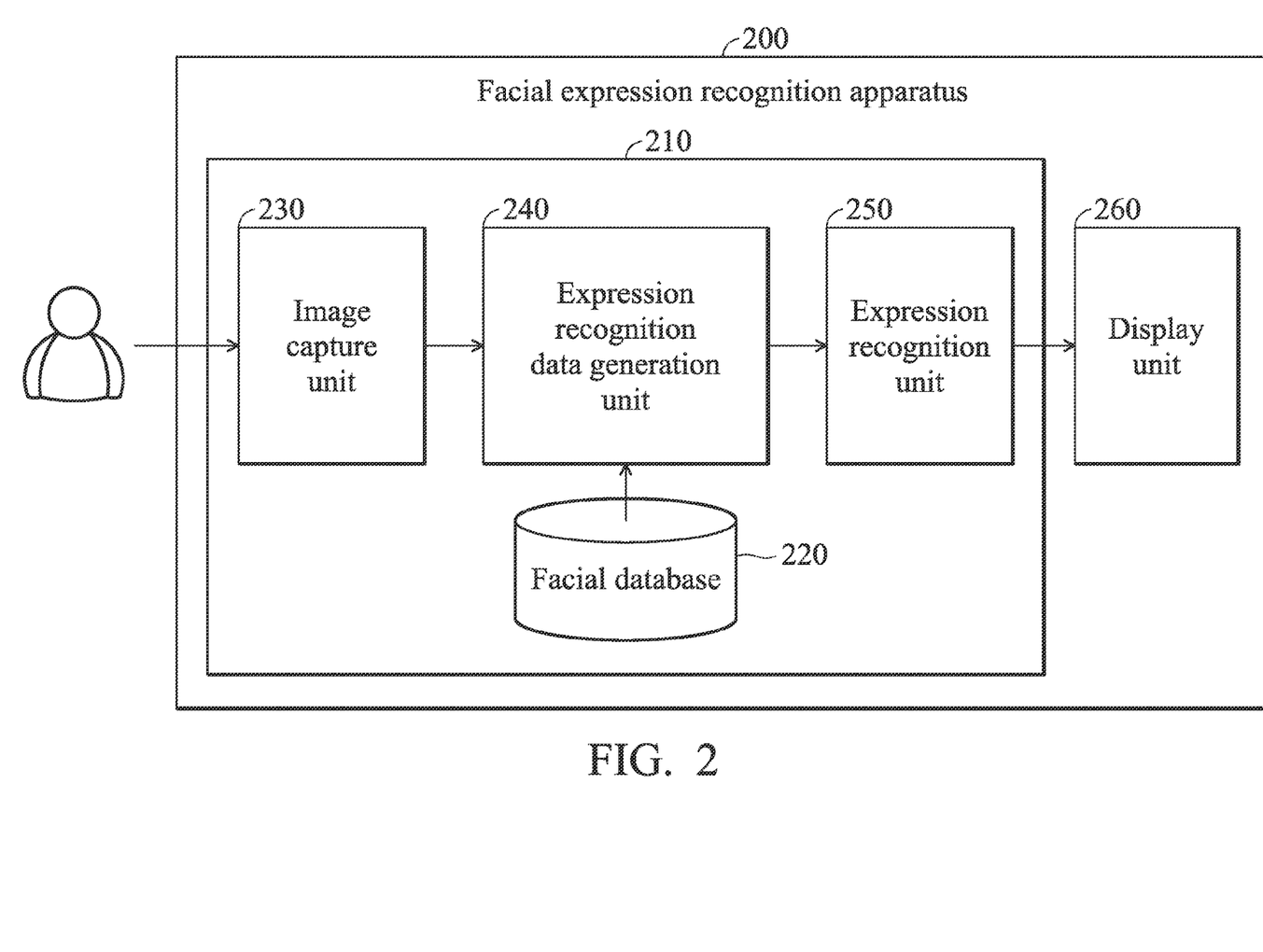
FIG. 2 is a schematic diagram illustrating an embodiment of a facial expression recognition apparatus of the invention.

FIG. 2 is a schematic diagram illustrating an embodiment of a facial expression recognition apparatus 200 of the invention. The facial expression recognition apparatus 200 is particularly suitable applied to a portable or hand-held electronic device, such as a mobile phone, a PDA, a mini-notebook or a laptop computer. The facial expression recognition apparatus 200 at least comprises a shell 210, a facial database 220, an image capture unit 230, an expression recognition data generation unit 240, an expression recognition unit 250 and a display unit 260. Functionalities of the facial database 220, the image capture unit 230, the expression recognition data generation unit 240 and the expression recognition unit 250 in the apparatus 200 are similar to those in the system 100 and thus detailed description is omitted here. The facial database 220, the image capture unit 230, the expression recognition data generation unit 240 and the expression recognition unit 250 may be contained inside the shell 210. The display unit 260 may be disposed outside the shell 210 or may link to the expression recognition unit 250 within the shell 210 through a wired/wireless connection. In other embodiments, the facial database 220 may be disposed outside the shell 210 and the facial expression recognition apparatus 200 may link to the facial database 220 through the wired/wireless connection.

Figure 3:
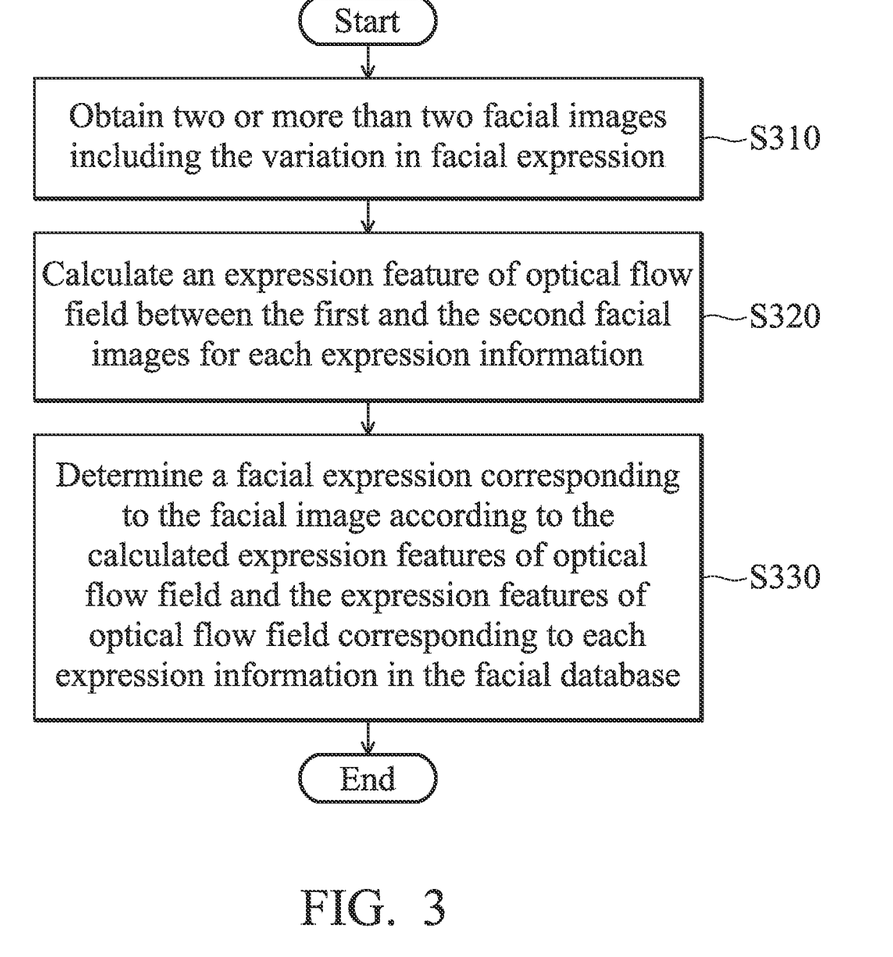
FIG. 3 is a flowchart illustrating an embodiment of a facial expression recognition method of the invention.

FIG. 3 is a flowchart illustrating an embodiment of a facial expression recognition method of the invention. The facial expression recognition method can be performed by the facial expression recognition system 100 shown in FIG. 1.

First, in step S310, the image capture unit 110 obtains two or more than two facial images including variations in facial expressions. In one embodiment, the image capture unit 110 may first receive a video sequence and then obtain two or more than two facial images from the video sequence. The video sequence may be continuous images captured in a certain period of time. Thereafter, in step S320, an expression feature of optical flow field between the first and the second facial images is calculated. The method for calculating the optical flow of the first and the facial images will be illustrated below. In this step, the expression recognition data generation unit 120 may calculate a variation in optical flow between the first and the second facial images and further utilize the calculated expression feature of optical flow field with the expression features of optical flow field in the facial database 140 for conversation, by the calculation module 124, to the corresponding feature.

In one embodiment, when the expression recognition data generation unit 120 calculates a variation in optical flow between the first and the second facial images, a facial calibration step may be further performed, by the calibration module 122, to correct the first and the second facial images. For example, the calibration module 122 may estimate a motion parameter by utilizing a position of the facial feature point, such as the five sense organs, of each of the first and the second facial images, and then adjust the first facial image to the second facial image by utilizing the calculated motion parameter. The detailed facial calibration step will be described below.

In one embodiment, when the calculation module 124 calculates the expression features of optical flow field between the first and the second facial images, it may utilize weighted masks each corresponding to a different expression to perform a weighted operation on the calculated variation in optical flow. Each weighted mask corresponding to each of the expression information may be obtained in advance by training on a large amount of facial expression image data which are served as the training data and the obtained weight masks may be further stored in the facial database or other storage mediums. For example, multiple expression faces for each kind of expression are first collected, wherein each expression face may correspond to a variation in optical flow, and then, by utilizing the variations in optical flow corresponding to the expression faces of each kind of expression, a weight mask corresponding to each kind of expression can be obtained by learning. Then, by utilizing the weight mask corresponding to each kind of expression, the expression features of optical flow field for the first facial image, the second facial image and each expression may be calculated. In one embodiment, by utilizing the training images, a facial important area corresponding to each of the expression information may be determined to generate a weight mask corresponding to each of the expression information, e.g., the expression features of optical flow field stored in the facial database may be generated based on a variation in optical flow between a non-expressional facial image and the representative facial image corresponding to each of the expression information and the weight mask corresponding thereto. The weight mask corresponding to each of the expression information may be generated by weighting the facial important area corresponding to each of the expression information. The related weight mask and the calculation for generating the expression features of optical flow field by the calculation module 124 utilizing the weight mask will be described below.

Then, in step S330, the expression recognition unit 130 may determine a facial expression corresponding to the facial image according to the expression features of optical flow field calculated by the expression recognition data generation unit 120 and the expression features of optical flow field corresponding to each expression information in the facial database 140, wherein each of the expression features of optical flow field corresponds to one of the expression information.

In this step, when the calculated expression feature of optical flow field is similar to one of the expression features of optical flow field in the facial database, the expression recognition unit 130 may determine, based on the expression information corresponding to the similar one of the expression features of optical flow field, that the facial expression corresponding to the facial image is the expression corresponding to the similar one of the expression feature of optical flow field. For example, if the calculated expression feature of optical flow field is similar to the expression features of optical cal flow field corresponding to the expression information "smile" of the facial database, then it is determined that the facial expression corresponding to the facial image is "smile".

Further, since each kind of expression may comprise one or more than one variation feature in optical flow, the facial database 140 may further store the corresponding weight mask of each of the expression information, wherein the expression features of optical flow field thereof may be further generated according to the expression feature of optical flow field between two facial images corresponding to each expression information and the respective weight mask of each expression information. The expression recognition data generation unit 120 may first calculate a variation in optical flow between the first and second facial images and then respectively calculate the expression features of optical flow field of each expression information corresponding to the first facial image and the second facial image by applying the weight mask of each expression information to the calculated expression feature of optical flow field.

For explanation, one specific embodiment is illustrated in the following, and those skilled in the art will understand that this specific embodiment is used for explanation only and the invention is not limited thereto.

Because the entire facial image is processed in this invention, the facial images which are respectively captured during different periods of time may differ in angle or size. In addition, due to affected by the background environment, the detected result of a human face is usually uncertain. In practice, it is impossible to calculate a useful optical flow of a facial expression which moves around and unstable. Thus, in some embodiments, prior to calculating the expression optical flow to serve as the expression recognition feature, it is necessary to perform an angular calibration on the facial feature point, such as a nose, by an image processing technology for correcting the facial image so that the image to be processed can be amended to have the same coordinates.

To achieve the calibration objective, the activity of facial image calibration may be completed by locating of the facial feature point such as the five sense organs. Because a nose is located on a facial portion that has a smaller probability of being affected by facial expressions or the environment, it is easier to be located. Thus, in this embodiment, the facial calibration step is performed based on the nose area, wherein the motion parameters of each facial image, for example, the scaling ratio, the moving direction, the rotation angle and so on, are estimated by utilizing the position of the nose, and then these motion parameters are used to adjust two faces respectively detected at two different time periods.

Figure 4:
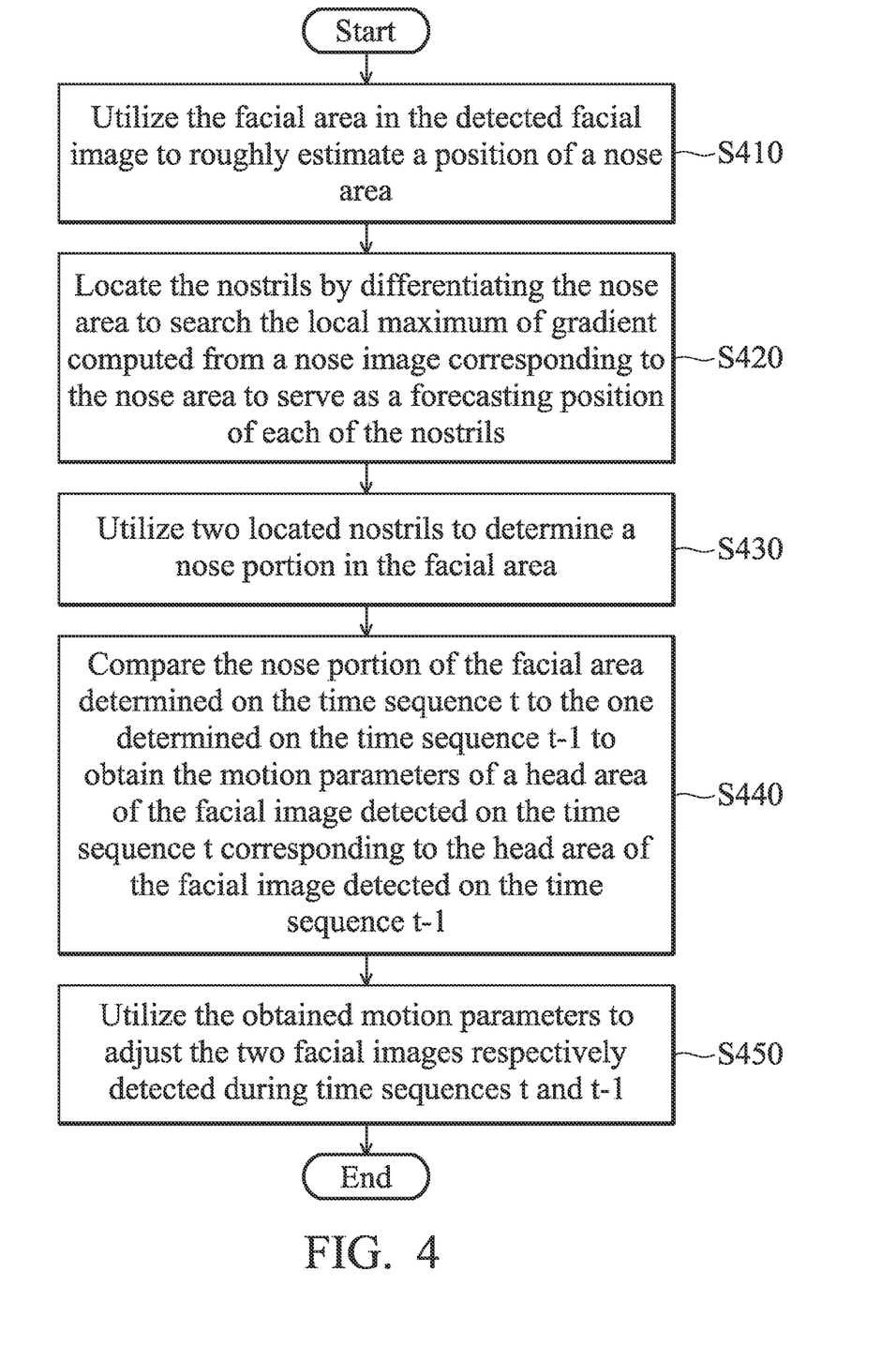
FIG. 4 is a flowchart illustrating an embodiment of the facial calibration steps based on the nose area of the invention.

FIG. 4 is a flowchart illustrating an embodiment of the facial calibration steps based on the nose area of the invention. The facial calibration steps based on the nose area of the invention can be performed by the calibration module 122 of the expression recognition data generation unit 120 in the facial expression recognition system 100 shown in FIG. 1.

First, in step S410, the calibration module 122 roughly estimates a position of a nose area by utilizing the facial area in the detected facial image. Then, in step S420, the calibration module 122 locates the nostrils by differentiating the nose area to search the local maximum of gradient computed from a nose image corresponding to the nose area to serve as a forecasting position of each of the nostrils. Next, in step S430, the calibration module 122 utilizes two located nostrils to determine a nose portion in the facial area, and, in step S440, the calibration module 122 compares the nose portion of the facial area determined on the time sequence t to the one determined on the time sequence t−1 to obtain the motion parameters of a head area of the facial image detected on the time sequence t corresponding to the head area of the facial image detected on the time sequence t−1, wherein the motion parameters may include but are not limited to, the scaling ratio, the moving direction, the rotation angle and so on for each one of the two facial images. Finally, in step S450, the calibration module 122 utilizes the obtained motion parameters to adjust the two facial images respectively detected during time sequences t and t−1.

Thus, with the aforementioned calibration steps based on the nose area, the motion factors of the entire head area may be eliminated so as to preferably estimate the expression optical flow caused by the motion of facial muscles.

During face detection, the positions of the face may differ from one frame to the other frame, and thus it is necessary to perform the aforementioned calibration steps to determine the feature points which may be used to correct the facial position in the subsequent facial detection procedure utilizing the optical flow so as to obtain a more accurate facial portion.

After the calibration steps based on the nose area have been performed, the expression recognition data generation unit 120 may further utilize the calculation module 124 to extract the expression information features, i.e. to generate the expression features of optical flow field. During the extraction, for a detected face x, the optical flow (expressed as OFx) thereof may firstly be calculated and then its weight similar to the $i^{th}$ mean optical flow (expressed by the function M(OFx, EXPi)) may be calculated. The method for training of the weight mask will be illustrated below. Referring to FIG. 5, which is a schematic diagram illustrating an embodiment of an averaged expression face together with its corresponding expression optical flow of the invention. As shown in FIG. 5, the corresponding expression optical flow $OF_1$-$OF_6$ respectively may be obtained by comparing the averaged expression faces 1-6 respectively to a normal face with no expressions 0.

Assume that the transformation procedures from a face with no expressions to a face with expression will be very similar, provided that they belong to the same type of expression. For example, when a human is smiling, the corners of the mouth corners are raised, which will be similar in terms of direction with the only difference in terms of the amount of level raised. On the other hand, for a human p, as to the expression optical flow ($OF_{intra,p\_k}$) respectively calculated in accordance with one of the different facial expressions k, a relatively larger difference in similarity will be obtained by comparing such different facial expressions k. Based on this assumption, in this embodiment, the similarity among faces which are with expressions can be estimated by comparing and aggregating the differences among the optical flow components.

Figure 6:
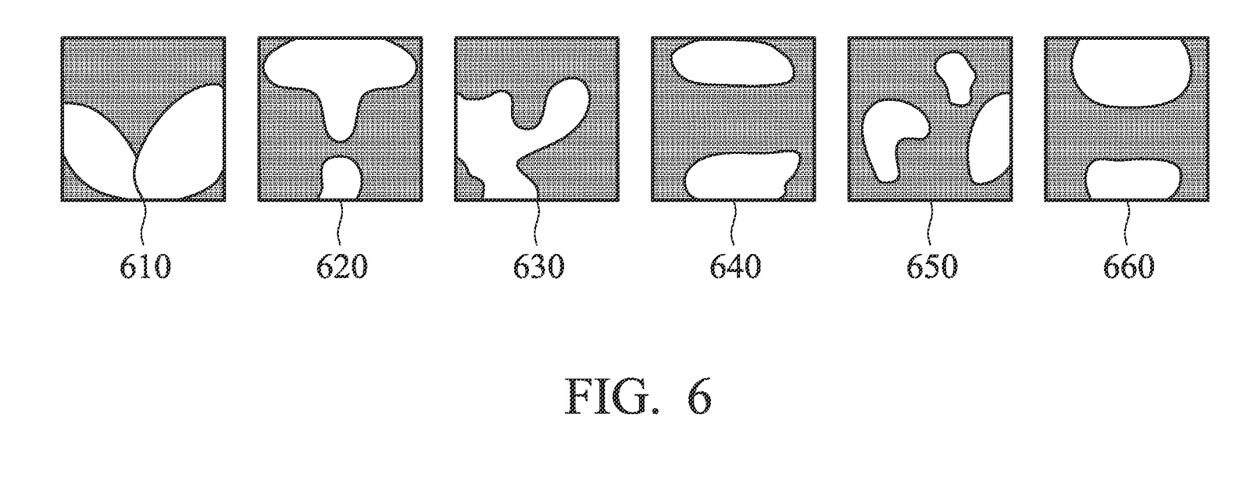
FIG. 6 illustrates an embodiment of weight masks for different facial expressions of the invention.

Generally, a different muscular movement in face may be inducted from the different expression. For example, the corners of a mouth will rise when smiling. Therefore, as for the expression optical flows respectively calculated from each of the faces with a similar expression shown in two images, the optical flow components each corresponding to the facial muscle are in the proximately similar direction. On the contrary, a similar local muscular movement of a face may be found in two different expressions, such as fear and disgust. For example, the inner sides of eyebrows will rise in both cases. If these two expressions have to be distinguished, confusion may be caused by the information obtained from the area of eyebrows. Thus, it has to be excluded. In one embodiment, a statistical learning method may be further utilized in this invention, wherein a facial area weight for each expression may be inducted by utilizing a large amount of training data via a quadratic programming method. Therefore, weight masks 610-660 for different expressions, as shown in FIG. 6, may be obtained by the aforementioned adjustment steps.

In this embodiment, an optimized problem is designed for each expression to more resiliently and automatically learn the weights from training data:

$$\min_{w,\xi,\rho} \alpha\left(\frac{1}{2} w^T Q w\right) - \frac{1}{m}\sum_{i=1}^{m}(w^T a_i - v\rho) + C\sum_{i=1}^{m} \xi_i \quad (1)$$

$$\text{s.t. } w^T a_i \geq \rho - \xi_i, \xi_i \geq 0, \rho \geq 0, i = 1, 2, \ldots, m,$$

wherein w is the weight which is desired to be determined, v is a reference for controlling the separation level among different expressions, and ξi are slack variables allowing for errors.

In order to achieve the balance between the data term in the left hand side of formula (1) and the smoothness term in its right hand side, in this embodiment, the reference a is utilized to balance the magnitude orders on the two sides, wherein $a_i$ is the column vector obtained in accordance with the following hypothesis: for a human face with a facial expression k, its expression optical flow obtained by calculating the weighting w, ($OF_{intra\_p\_k}$), shall be similar to the mean expression optical flow of the same class ($OF_{intra,mean\_k}$) and shall not be similar to the mean expression optical flow of the different class ($OF_{intra,mean\_t}$) for all k not equal to t.

Precisely, for the column vector $a_i$, the $j^{th}$ component thereof ($M_j$) may be calculated in accordance with the following formula: (8)

$$a_{ji} = \begin{cases} M_j(OF_{intra,p\_k}, OF_{intra,mean\_k}) - M_j(OF_{intra,p\_k}, OF_{intra,mean\_t}) \\ M_j(OF_{intra,p\_t}, OF_{intra,mean\_t}) - M_j(OF_{intra,p\_t}, OF_{intra,mean\_k}) \end{cases} \quad (2)$$

It should be noted that the aforementioned formula (1) represents an optimized problem. That is, a quadratic programming problem for which a universal optimal solution may be found.

Figure 7:
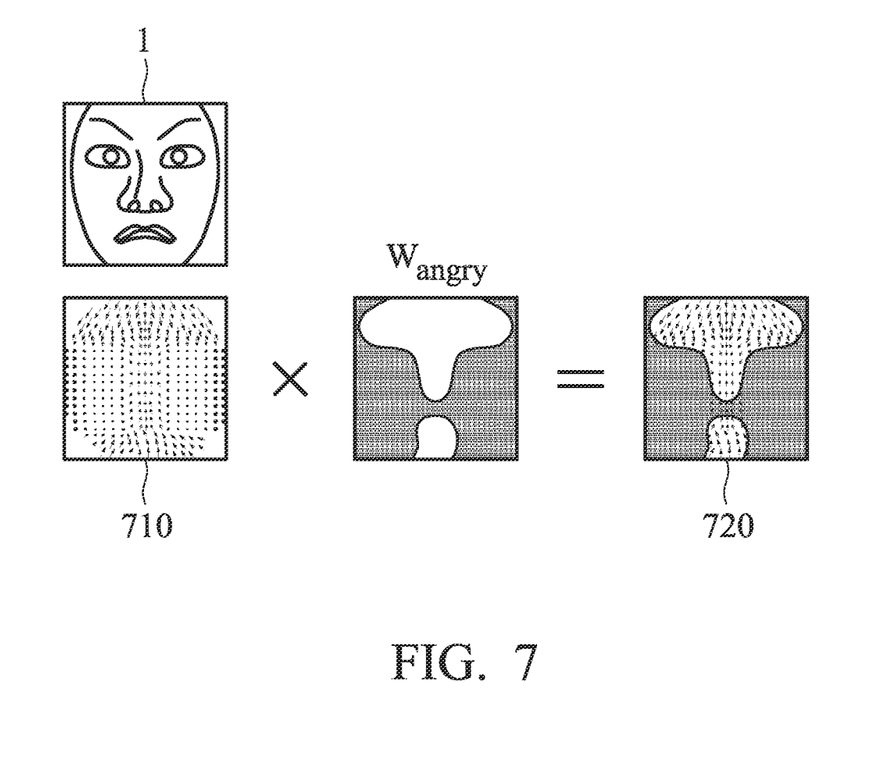
FIG. 7 is a schematic diagram illustrating an embodiment of the invention, which applies a trained weighted face corresponding to a facial expression to the expression optical flow.

Thus, in accordance with formula (1), a corresponding weighted face that corresponds to each kind of expression may be obtained by training each kind of expression. Referring to FIG. 7, FIG. 7 is a schematic diagram illustrating an embodiment of the invention, which applies a trained weighted face corresponding to the expression "angry" to the expression optical flow. As shown in FIG. 7, for the weighted expression optical flow 720 of the expression "angry" obtained by weighting the expression optical flow 710 with utilizing the weight mask "$w_{angry}$", only the expression features of optical flow field for its facial importance areas will be reserved.

Each expression will possess a distinguishable facial muscular presentation (that is, different variations in optical flow) from that of other expressions. Thus, most discriminating feature areas for each kind of expression may be determined and a weight mask may be generated based on them to improve the accuracy in calculating the similarity of expressions.

Therefore, for a detected face x, its weighted expression optical flow ($OF_{intra,x}$) may be calculated firstly, and then its weighted similarity to the mean expression optical flow may be calculated by $M(OF_{intra,x}, OF_{intra,mean\_k})$. To achieve a better discrimination ratio during the expression recognition, the weighted difference of each kind of different facial expressions for each face x may be calculated and then low-dimensional feature vectors with a better discrimination ratio may be extracted from it.

The extracted lower-dimensional feature vectors may be used to train the expression recognition unit 130 (for example, a classifier). More particularly, if the classifier totally classifies k kinds of expression, for a detected face, a function $\Phi: \mathfrak{R}^d \mapsto \mathfrak{R}^{K(K-1)}$ may be defined to transform it into a set of vectors in K×(K−1) dimension:

$$OF_{intra,x}=(x_1,x_2,\ldots,x_d) \mapsto \Phi(x)=(\phi_1(x),\phi_2(x),\ldots,\phi_n(x),\ldots) \quad (3),$$

wherein xi represents the ith component, and the nth dimension of $\Phi(x)$ may be defined as follows:

$$\phi_n = w_k^T(\tilde{M}^k(OF_{intra,x},OF_{intra,mean\_k}) - \tilde{M}^t(OF_{intra,x},OF_{intra,mean})) \forall k \neq t, \tilde{M}^k = \beta_k \times M \quad (4),$$

wherein $\beta_k$ is a constant which is used to balance the expression intensity to a roughly equal ratio in the experiment. In this embodiment, the expression optical flow can be calculated by utilizing the same image database used in the training weight mask and the expression recognition unit 130 can be trained by the feature vector which is transformed into low-dimension by formula (3).

In summary, according to the facial expression recognition system and method thereof of the invention, a facial expression recognition based on a facial image or on a video sequence may be performed such that the expression feature of optical flow field between two facial images or continuous facial images respectively obtained during certain time periods can be compared with the expression feature of optical flow field among all possible expressions existing in a facial database and its expression can be predicted in accordance with the compassion result. Furthermore, with the facial expression recognition system and method thereof of the invention, a human facial angular calibration may be performed based on the feature of the expression optical flow through the facial feature point such as the nostrils positions, to mitigate uncertainty in facial detecting components, such that the calculated expression optical flow can be more accurate. Moreover, level of importance of a human face area to the different expression area can be optimized through training to generate a corresponding weight mask, and then each one of the expressions may be weighted by the weight mask to classify the expression with higher efficiency.

While the invention has been described by way of example and in terms of preferred embodiment, it is to be understood that the invention is not limited thereto. Those who are skilled in this technology can still make various alterations and modifications without departing from the scope and spirit of this invention (e.g., use a ring buffer). Therefore, the scope of the present invention shall be defined and protected by the following claims and their equivalents.

What is claimed is:

1. A facial expression recognition method, comprising:
    receiving a first facial image and a second facial image;
    calculating an expression feature of optical flow field between the first facial image and the second facial image corresponding to each of a plurality of expression information respectively; and
    determining a facial expression corresponding to the first and second facial images according to the calculated expression feature of optical flow field for each of the plurality of expression information and a plurality of the expression features of optical flow field in a facial database, wherein the facial database comprises the plurality of expression information and the plurality of expression features of optical flow field, and wherein each of the expression features of optical flow field corresponds to one of the plurality of expression information,
    wherein the facial database further comprises a weight mask corresponding to each of the plurality of expression information and the step of calculating the expression feature of optical flow field further comprises:
    generating the calculated expression feature of optical flow field according to the expression feature of optical flow field between the first facial image and the second facial image and the weight mask corresponding to each of the plurality of expression information.

2. The facial expression recognition method of claim 1, wherein the step of calculating the expression feature of optical flow field between the first facial image and the second facial image further performs a facial calibration step for adjusting the first facial image to the second facial image.

3. The facial expression recognition method of claim 2, wherein the facial calibration step further comprises:
    estimating a motion parameter by utilizing a position of a facial feature point of the first facial image and the second facial image respectively; and
    adjusting the first facial image to the second facial image by utilizing the calculated motion parameter.

4. The facial expression recognition method of claim 3, wherein the step of adjusting the first facial image to the second facial image further comprises:
    utilizing a facial area in the second facial image to roughly estimate a position of a nose area thereof;
    locating the nostrils by differentiating the nose area to search the local maximum of gradient computed from a nose image corresponding to the nose area;
    utilizing the located nostrils to determine a nose portion of the second facial image; and
    comparing the nose portion of the second facial image to a previously calculated nose portion of the first facial image to obtain the motion parameters of the second image that correspond to a head area of the first facial image and adjusting the second facial image to the first facial image according to the obtained motion parameters.

5. The facial expression recognition method of claim 3, wherein the motion parameters of the first and the second facial images comprise the scaling ratio, the moving direction and the rotation angle.

6. The facial expression recognition method of claim 1, further comprising:
    determining a facial important area corresponding to each of the expression information; and
    weighting the facial important area to generate a weight mask corresponding to each of the expression information.

7. The facial expression recognition method of claim 1, further comprising:
    determining whether the calculated expression feature of optical flow field is similar to one of the plurality of expression features of optical flow field in the facial database; and
    if the calculated variation in optical flow is similar to one of the plurality of expression features of optical flow field in the facial database, determining that the expression of the similar one of the expression features in the facial database is the facial expression corresponding to the first and the second facial images.

8. The facial expression recognition method of claim 1, wherein the step of determining the facial expression corresponding to the facial images is performed by utilizing a classifier to determine the corresponding facial expression from the expression information and the variation features in optical flow in the facial database.

9. A facial expression recognition system, comprising:
   a facial database, including a plurality of expression information and a plurality of expression features of optical flow field, wherein each of the expression features of optical flow field corresponds to one of the plurality of expression information;
   an image capture unit, capturing a plurality of facial images;
   an expression recognition data generation unit coupled to the image capture unit and the facial database, receiving a first facial image and a second facial image from the image capture unit and calculating an expression feature of optical flow field between the first facial image and the second facial image corresponding to each of the plurality of expression information respectively; and
   an expression recognition unit coupled to the expression recognition data generation unit, determining a facial expression corresponding to the first and second facial images according to the calculated expression feature of optical flow field for each of the plurality of expression information and the variation features in optical flow in the facial database,
   wherein the facial database further comprises a weight mask corresponding to each of the plurality of expression information and the expression recognition data generation unit further generates the calculated expression feature of optical flow field according to the expression feature of optical flow field between the first facial image and the second facial image and the weight mask corresponding to each of the plurality of expression information.

10. The facial expression recognition system of claim 9, wherein the expression recognition data generation unit further comprises a calibration module for performing a facial calibration step to adjust the first facial image to the second facial image when calculating the expression features of optical flow field between the first facial image and the second facial image.

11. The facial expression recognition system of claim 10, wherein the calibration module further estimates a motion parameter by utilizing a position of a facial feature point of the first and the second facial images and adjusts the first facial image to the second facial image by utilizing the calculated motion parameter to perform the facial calibration.

12. The facial expression recognition system of claim 11, wherein the calibration module further utilizes a facial area in the second facial image to roughly estimate a position of a nose area thereof, locates the nostrils by differentiating the nose area to search the local maximum of a gradient nose corresponding to the nose area, utilizes the located nostrils to determine a nose portion of the second facial image and compares the nose portion of the second facial image to a previously calculated nose portion of the first facial image to obtain the motion parameters of the second image that correspond to a head area of the first facial image and adjusts the second facial image to the first facial image according to the obtained motion parameters.

13. The facial expression recognition system of claim 11, wherein the motion parameters of the first and the second facial images comprise the scaling ratio, the moving direction and the rotation angle.

14. The facial expression recognition system of claim 9, wherein the weight mask corresponding to each of the expression information is generated by weighting a facial important area corresponding to each of the expression information.

15. The facial expression recognition system of claim 9, wherein the expression recognition unit further determines whether the calculated expression feature of optical flow field is similar to one of the plurality of expression features of optical flow field in the facial database, and determines that the expression of the similar one of the expression features in the facial database is the facial expression corresponding to the first and the second facial images if the calculated variation in optical flow is similar to one of the plurality of expression features of optical flow field of the one of the expression features of the facial database.

16. The facial expression recognition system of claim 9, wherein the expression recognition unit is a classifier for determining the corresponding facial expression from the expression information and the variation features in optical flow in the facial database.

17. A facial expression recognition apparatus, comprising:
   a shell;
   a facial database disposed inside of the shell, including a plurality of expression information and a plurality of expression features of optical flow field, wherein each of the expression features of optical flow field corresponds to one of the plurality of expression information;
   an image capture unit disposed inside of the shell, capturing a plurality of facial images;
   an expression recognition data generation unit disposed inside of the shell and coupled to the image capture unit and the facial database, receiving a first facial image and a second facial image from the image capture unit and calculating an expression feature of optical flow field between the first facial image and the second facial image corresponding to each of the plurality of expression information respectively;
   an expression recognition unit disposed inside of the shell and coupled to the expression recognition data generation unit, determining a facial expression corresponding to the first and second facial images according to the calculated expression feature of optical flow field for each of the plurality of expression information and the variation features in optical flow in the facial database; and
   a display unit disposed outside of the shell and coupled to the expression recognition unit for displaying a result corresponding to the determined facial expression,
   wherein the facial database further comprises a weight mask corresponding to each of the plurality of expression information and the expression recognition data generation unit further generates the calculated expression feature of optical flow field according to the expression feature of optical flow field between the first facial image and the second facial image and the weight mask corresponding to each of the plurality of expression information.

18. A non-transitory computer-readable storage medium storing a computer program, which, when executed, causes a device to perform a facial expression recognition method, and the method comprising:
   receiving a first facial image and a second facial image;
   calculating an expression feature of optical flow field between the first facial image and the second facial image corresponding to each of a plurality of expression information respectively; and
   determining a facial expression corresponding to the first and second facial images according to the calculated expression feature of optical flow field for each of the plurality of expression information and a plurality of the expression features of optical flow field in a facial database, wherein the facial database comprises the plurality of expression information and the plurality of expression features of optical flow field, and wherein each of the expression features of optical flow field corresponds to one of the plurality of expression information, wherein the facial database further comprises a weight mask corresponding to each of the plurality of expression information and the step of calculating the expression feature of optical flow field further comprises:

generating the calculated expression feature of optical flow field according to the expression feature of optical flow field between the first facial image and the second facial image and the weight mask corresponding to each of the plurality of expression information.

* * * * *